United States Patent [19]

Junek et al.

[11] 4,212,818

[45] Jul. 15, 1980

[54] PROCESS FOR THE PRODUCTION OF AMINOMALONIC ACID DINITRILE AS AN AMINOMALONIC ACID DINITRILTOSYLATE PRECIPITATE OR AS AN ACETYLAMINOMALODINITRILE PRECIPITATE

[75] Inventors: Hans Junek; Martin Mittelbach, both of Graz, Austria

[73] Assignee: Lonza Ltd., Gampel, Switzerland

[21] Appl. No.: 4,842

[22] Filed: Jan. 19, 1979

[30] Foreign Application Priority Data

Jan. 20, 1978 [CH] Switzerland .............................. 611/78

[51] Int. Cl.$^2$ .................... C07C 121/42; C07C 121/60
[52] U.S. Cl. .............................. 260/465.4; 260/465 E; 260/465.5 R
[58] Field of Search ...................... 260/465.5 R, 465.4, 260/465 E

[56] References Cited

U.S. PATENT DOCUMENTS

| 3,670,007 | 6/1972 | Ferris | 260/465.5 R |
| 3,810,935 | 5/1974 | Leimgruber et al. | 260/465.5 R |

FOREIGN PATENT DOCUMENTS 599127  5/1960  Canada ................................ 260/465.5

OTHER PUBLICATIONS

Ferris et al., J.A.C.S., 87 (1965), pp. 4976–4977.
Ferris et al., J.A.C.S., 88 (1966), pp. 3829–3831.
C.A., 77, 100866v (1972), Ferris.
Ferris, et al., Org. Syn., 48, pp. 1–3, (1970).

*Primary Examiner*—Joseph Paul Brust
*Attorney, Agent, or Firm*—Fisher, Christen & Sabol

[57] ABSTRACT

Process for the production of aminomalonic acid dinitrile from a malonic acid dinitrile compound, such as oximinomalonic acid dinitrile or phenylazomalonic acid dinitrile. The reaction is carried out at an elevated hydrogen pressure in the presence of Raney catalysts and a solvent. When tetrahydrofurane is used as a solvent, the reaction product is precipitated with p-toluene sulfonic acid. When acetic anhydride is used as solvent, the reaction product is precipitated as acetyl aminomalonic acid dinitrile.

11 Claims, No Drawings

PROCESS FOR THE PRODUCTION OF AMINOMALONIC ACID DINITRILE AS AN AMINOMALONIC ACID DINITRILTOSYLATE PRECIPITATE OR AS AN ACETYLAMINOMALODINITRILE PRECIPITATE

BACKGROUND OF THE INVENTION

1. Field Of The Invention

The invention relates to a process for the production of aminomalonic acid dinitrile.

2. Prior Art

It is known to isolate aminomalonic acid dinitrile as the p-toluene sulfate by reduction of oximinomalonic acid dinitrile with aluminum amalgam. This production, however, is time consuming and cumbersome. The amalgamation of the aluminum causes difficulties, since the mercury layer on the surface of the aluminum does not adhere well. Moreover, during sucking off of the aluminum hydroxide after the reduction, much of the product remains behind in the deposit (precipitate) (J. P. Ferris, L. E. Orgel, J. Am. Chem. Soc. 87, 4976-7 (1965); J. P. Ferris, L. E. Orgel, J. Am. Chem. Soc. 88, 3829-31 (1966); J. P. Ferris, U.S. Pat. No. 3,670,007 (1972), C. A. 77, 100866v (1972); J. P. Ferris, R. A. Sanchez, R. W. Mancuso, Org. Synth. 48, 1-3).

In U.S. Pat. No. 3,670,007, it is also disclosed that oximinomalonitrile or phenazomalonitrile can be reduced with zinc, sodium or aluminum dithionite in the presence of acid to form aminomalonitrile. However, the process is limited to the quantitative proof of aminomalonic acid dinitrile in the reaction solution.

BROAD DESCRIPTION OF THIS INVENTION

An object of this invention is to provide a process for the production of aminomalonic acid dinitrile which will permit one to both avoid the disadvantages of the process which uses aluminum amalgam and, to manufacture the product in a simple manner. It is a further object of the present invention to produce aminomalonic acid dinitrile in high yields.

According to the present invention the objects and advantages of this invention are achieved by converting a malonic acid dinitrile reactant to aminomalonic acid dinitrile by reducing the malonic acid dinitrile reactant with hydrogen at a hydrogen pressure of about 4 to 6 atmospheres and at temperatures of about 10° to 80° C. in the presence of a Raney catalyst and a solvent, and precipitating and isolating the resulting aminomalonic acid dinitrile.

Suitable starting compounds are oximinomalonic acid dinitrile, or phenylazomalonic acid dinitrile. Suitable solvents are tetrahydrofurane and acetic anhydride.

For example, the reaction may be carried out with oximinomalonic acid dinitrile which is produced by reacting malonic acid dinitrile in glacial acetic acid with sodium nitrite dissolved in water, at temperatures around 0° C., and by extracting with ether. The reaction mixture may then be admixed with tetrahydrofurane and the ether may be distilled away. The tetrahydrofurane solution containing oximinomalonic acid dinitrile is reacted further in accordance with the teachings of the present invention.

The Raney catalyst which effectively contains Ni, Fe, Cu and/or Co, is added to the tetrahydrofurane solution. The oximinomalonic acid dinitrile is reduced at hydrogen pressures of 4 to 6 atmospheres and temperatures of 10° to 80° C. within a time of 1 to 10 hours. Typically, 60 to 80 g, preferably 70 g, of catalyst is used per mole of malonic acid dinitrile.

After removal of the catalyst, p-toluene sulfonic acid in ether is added to the reaction mixture and after about 1 to 20 hours, the deposit developed from aminomalonic acid dinitrile tosylate is isolated from the reaction mixture. In a preferred embodiment, the p-toluene sulfonic acid is added to the reaction mixture in two fractions, whereby 0.02 to 0.03 mole of p-toluene sulfonic acid may be used in the first fraction and 0.03 to 0.1 mole of p-toluene sulfonic acid may be used in the second fraction, each per 0.1 mole of malonic acid dinitrile. The first deposit contains the impurities and is thrown away.

Whenever phenylazomalonic acid dinitrile is reduced with Raney nickel in tetrahydrofurane, aniline and aminomalonic acid dinitrile develop as end products, which may be precipitated jointly as the p-toluene sulfonates. When acetic anhydride is used as a solvent, the acyl derivatives of the two amines are produced.

DETAILED DESCRIPTION OF THE INVENTION

As used herein, all parts, ratios and percentages are on a weight basis unless otherwise stated herein or otherwise obvious herefrom to one ordinarily skilled in the art.

EXAMPLE 1

Production of the oximinomalonic acid dinitrile:

6.6 g (0.1 mole) of malonic acid dinitrile are dissolved in 20 ml of glacial acetic acid and are cooled down to 0° C. with a glacial mixture of sodium chloride. A solution of 12.5 g (0.18 mole) of sodium nitrite in 20 ml of water is added drop by drop over a period of 30 minutes at a temperature of 0° C. Stirring is continued while cooling in an ice bath for 4 hours and subsequently, it is extracted twice each time with 50 ml of ether. The volatile solution is dried with sodium sulfate, is filtered and mixed with 100 ml of absolute tetrahydrofurane. After that, the ether (100 ml) is distilled off by application of a vacuum (12 mm, no heating necessary).

Production of the aminomalonic acid dinitrile:

The tetrahydrofurane solution is reduced subsequently with 7 g of Raney nickel (puriss, Fluka) at a hydrogen pressure of 4 atm for 4 hours at 20° C. After sucking off the catalyst and concentrating to 100 ml, 5 g (26.3 m mole) of p-toluene sulfonic acid in 20 ml of ether are added and the precipitate developed is thrown away. The filtrate is mixed with an additional 15 g of p-toluene sulfonic acid in 50 ml of ether. This is filled up with ether to 250 ml and it is allowed to stand for 12 hours at about 4° C. The deposit of aminomalonic acid dinitriltosylate which forms, is sucked off and washed secondarily with ice-cold acetonitrile and ether. It is dried in a vacuum desiccator at 20° C. Yield 12.2 g (49% of theory), melting point 165° C.

Recrystallization: acetonitrile melting point 175° C. (melting point, literature 169° C.)

$C_{10}H_{11}N_3O_3S$ (253.3) calculated: C 47.42; H 4.38; N 16.59; S 12.66; found: C 47.32; H 4.44; N 15.98; S 13.33.

$^1$H-NMR (DMSO): 2.23 ppm (s,$CH_3$), 6.00 ppm (s,CH), 8.10 ppm (s,$NH_3^+$), 7.22 ppm (q, aromatic)

EXAMPLE 2

5.1 g of phenylazomalodinitrile (0.03 mole) are dissolved in 100 ml of absolute tetrahydrofurane and are mixed with about 10 g of Raney nickel. Subsequently, this is reduced at a hydrogen pressure of 4 atm for 6 hours at 22° C. After sucking off the catalyst, 20 g (0.13 mole) of p-toluenesulfonic acid in 50 ml of ether are added to the filtrate and the resulting deposit of a mixture of aminomalonic acid dinitrile and aniline tosylates is sucked off. Yield 5 g (31% of theory).

EXAMPLE 3

5.1 g (0.03 mole) of phenylazomalodinitrile are dissolved in 100 ml of acetic anhydride and are mixed with about 10 g of Raney nickel. This is reduced at a hydrogen pressure of 4 atm for 6 hours at 35° C. The catalyst is sucked off, the filtrate is concentrated and the oil which develops is treated with water. The precipitate which is formed consists of a mixture of acetyl aminomalodinitrile and acetanilide, and may be separated by thin layer chromatography (glacial acetic acid: benzol—1:10). Yield 2.5 g (27% of theory).

We claim:

1. A process for the production of aminomalonic acid dinitrile as an aminomalonic acid dinitriltosylate precipitate or as an acetylaminomalodinitrile precipitate comprising converting a malonic acid dinitrile reactant selected from the group consisting of oximinomalonic acid dinitrile and phenylazomalonic acid dinitrile to aminomalonic acid dinitrile by reducing the malonic acid dinitrile reactant with hydrogen at a hydrogen pressure of about 4 to 6 atmospheres and at temperatures of about 10° to 80° C. in the presence of a Raney nickel catalyst and a solvent selected from the group consisting of tetrahydrofurane and acetic anhydride, and precipitating and isolating the resulting aminomalonic acid dinitrile as a precipitate selected from the group consisting of aminomalonic acid dinitriltosylate and acetylaminomalodinitrile, said aminomalonic acid dinitriltosylate being precipitated by treating the resulting aminomalonic dinitrile with p-toluenesulfonic acid.

2. A process as claimed in claim 1 wherein said solvent is tetrahydrofurane and said resulting aminomalonic acid dinitrile is precipitated by treatment with p-toluene sulfonic acid and the precipitate is isolated from the reaction mixture.

3. A process as claimed in claim 1 wherein said solvent is acetic anhydride and said resulting aminomalonic acid dinitrile is precipitated and isolated as acetyl aminomalonic acid dinitrile.

4. A process as claimed in claim 2 wherein said treatment with toluene sulfonic acid comprises adding the p-toluene sulfonic acid to the reaction mixture in two fractions, the first fraction containing 0.02 mole to 0.03 mole of p-toluene sulfonic acid per 0.1 mole of malonic acid dinitrile reactant, the second fraction containing 0.03 mole to 0.1 mole of p-toluene sulfonic acid per 0.1 mole of malonic acid dinitrile reactant.

5. A process as claimed in claim 1 wherein said malonic acid dinitrile reactant is oximinomalonic acid dinitrile.

6. The process as claimed in claim 1 wherein said malonic acid dinitrile reactant is phenylazomalonic acid dinitrile.

7. The process as claimed in claim 1, 5, or 6 wherein said Raney nickel catalyst consists essentially of Ni, Fe, Cu and/or Co.

8. The process as claimed in claim 7 wherein the Raney catalyst is used in an amount of 60 to 80 grams per mole of malonic acid dinitrile reactant.

9. a process as claimed in claim 3 wherein said Raney nickel catalyst consists essentially of Ni, Fe, Cu and/or Co and is used in an amount of 60 to 80 grams per mole of malonic acid dinitrile reactant.

10. A process as claimed in claim 4 wherein said Raney nickel catalyst consists essentially of Ni, Fe, Cu and/or Co and is used in an amount of 60 to 80 grams per mole of malonic acid dinitrile reactant.

11. A process as claimed in claim 1 wherein said reduction is conducted within a time of 1 to 10 hours.

* * * * *